US006544390B2

(12) United States Patent
Sinha et al.

(10) Patent No.: US 6,544,390 B2
(45) Date of Patent: Apr. 8, 2003

(54) MICROWAVE ASSISTED RAPID AND ECONOMICAL PROCESS FOR THE PREPARATION OF SUBSTITUTED PHENYLALDEHYDES FROM TRANS AND CIS-PHENYLPROPENES: A COMMERCIAL UTILISATION OF TOXIC CIS-ISOMER (75) Inventors: Arun Kumar Sinha, Himachal Pradesh (IN); Bhupendra Prasad Joshi, Himachal Pradesh (IN); Ruchi Dogra, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/823,123

(22) Filed: Mar. 30, 2001

(65) Prior Publication Data
US 2002/0153240 A1 Oct. 24, 2002

(51) Int. Cl.[7] ............................................. C07C 45/00
(52) U.S. Cl. .................................................. 204/157.93
(58) Field of Search ..................................... 204/157.93

(56) References Cited

PUBLICATIONS

Le et al. ("Oxidation of Anethole in Dry Media and Microwave Irradiation", Tap Chi Hoa Hoc (no month available, 1998), vol. 36, No. 2, pp. 70–73).**

Gracza et al. ("Photochemical Reactivity of Trans–Isoasarone and Related Phenylpropane Derivatives. Part 2. Stability and Durability of Phenylpropane Containing Pharmaceutical Preparations. Part 14. Active Principles of Asarum Europaeum L", Dtsch. Apoth.–Ztg. (no month available, 1981), vol. 121, No. 46, pp. 2541–2544). **
* Abstract Only.*

* cited by examiner

Primary Examiner—Edna Wong
(74) Attorney, Agent, or Firm—Jordan and Hamburg LLP (57) ABSTRACT

The present invention provides microwave assisted rapid and economical process for the preparation of substituted phenylaldehydes from trans and cis-phenylpropene, a commercial utilization of toxic cis-isomer of the general formula (I)

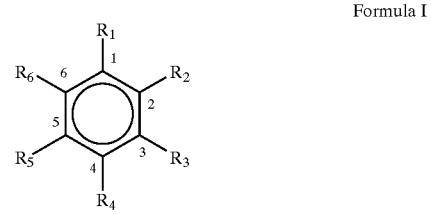

Formula I using meta-periodate and osmium tetraoxide (catalytic amount) as an efficient oxidizing agent in the presence of catalyst namely amberlite IRA-410 and quaternary ammonium salt.

18 Claims, 3 Drawing Sheets

¹H NMR (300 MHz)
SPECTRA OF 2,4,5-TRIMETHOXYBENZALDEHYDE IN CDCl₃

FIG. 1

MICROWAVE ASSISTED RAPID AND ECONOMICAL PROCESS FOR THE PREPARATION OF SUBSTITUTED PHENYLALDEHYDES FROM TRANS AND CIS-PHENYLPROPENES: A COMMERCIAL UTILISATION OF TOXIC CIS-ISOMER

FIELD OF THE INVENTION

The present invention relates to "microwave assisted rapid and economical process for the preparation of substituted phenylaldehydes from trans and toxic cis-phenylpropenes: a commercial utilization of toxic cis-isomer" in which industrially important phenylaldehydes (e.g. asaronaldehyde where $R_1$ is CHO, $R_2=R_4=R_5$ is —OMe and $R_3=R_6$ is H; p-anisaldehyde where, $R_1$ is —CHO, $R_2=R_3=R_5=R_6$ is H and $R_4$ is —OMe and vetralaldehyde where $R_1$ is —CHO, $R_2=R_5=R_6$ is H; $R_3=R_4$ is —OMe or the like) of the formula I Formula I are obtained via oxidation of easily available isomeric forms (trans and cis-isomer) of ($R_2$—$R_3$—$R_4$—$R_5$—$R_6$) phenylpropene bearing essential oils (i.e. β-asarone, anethole, and methyl isoeugenol or the like) wherein $R_2$ to $R_6$ equal or different, being hydrogen or hydroxy or acyl or alkyl or methylenedioxy or alkoxy groups or the like, under microwave irradiation using meta-periodate/osmium tetraoxide (catalytic amount) for a reaction time less than 20 minutes in biphasic system comprising a solvent and aqueous phase containing a catalyst (such as quaternary ammonium salt and amberlite IRA-410 etc) with high yield varying from 71–82% depending upon the reagent, reaction time, condition and the phenylpropene used. In addition crude *Acorus calamus* oil (rich in β-asarone present in 70–94%) used directly for microwave assisted oxidation is an added benefit as remaining constituents of *calamus* oil do not interfere for the preparation of asaronaldehyde (yield just less by 5–10% depending upon asarone percentage in *calamus* oil) which makes the above process further cost effective since tetraploid and hexaploid varieties of *Acorus calamus* has been internationally banned for their use in human consumption. Moreover, we have observed that the preparation of asaronaldehyde (a versatile drugs precursor) requires lesser time (2–20 minutes) under microwave irradiation while oxidation takes 2–6 hours when conducted at room temperature (conventional method).

BACKGROUND OF THE INVENTION

Naturally occurring substituted phenylaldehydes (Harborne, J. B. and Baxter, H., In: Phytochemical Dictionary, A Handbook of Bioactive Compounds from Plants, Taylor & Francis Ltd., London WC1N 2ET, 472–488 (1993)) e.g. vanillin, p-anisaldehyde, p-hydroxybenzaldehyde, asaronaldehyde, heliotropin and vetralaldehyde etc possess in common an aromatic ring bearing one or more hydroxy or dioxymethylene or alkoxy groups or the like, attached to a aldehyde group (CHO) contribute significantly to the taste and flavour of many foods, drinks, perfumery and serve as a pharmaceutical aid. In addition, phenylaldehyde derivatives serve as a raw material for the preparation of a large number of aromatic compounds useful in the perfume industry e.g. treatment of phenylaldehyde with alkali alcoholate results in the formation of phenyl benzoate and condensation of phenylaldehyde derivative with acetaldehyde gives cinnamic aldehyde which are useful in both the perfume and pharmaceutical industries. In addition, large quantities of phenylaldehydes are used in the manufacture of dyes, medicines (Patel, P. J.; Messer Jr., W. S. and Hudson, R. A., J. Med. Chem., 36, 1893–1901 (1993)), photographic films, cosmetics, dyes, agrochemicals etc.

The widespread aromatic aldehydes such as vanillin is obtained from the pods of *Vanilla planifolia* (family: Orchidaceae), the bulbs of Dahlia spp. (Compositae), the sprouts of Asparagus spp. (Liliaceae), the beats of Beta spp. (Chenopodiaceae) and also from the essential oils of *Syzygium aromaticum* (Myrtaceae), Ruta spp. (Rutaceae), Spiraea spp. (Rosaceae) and Gymnadenia spp. (Orchidaceae), while 3,4-methylenedioxybenzaldehyde (heliotropin) is obtained from the essential oils of the flowers and leaves of *Robinia pseudacacia* (Legumminosae), *Doryphora sassafras, Eryngium potericum* (Umbelliferae), Heliotropium spp. (Boraginaceae), Vanilla spp. (Orchidaceae) and from extracts of Viola spp. (Violaceae) and *Baccharis rosmarinifolia* (Compositae). Other phenylaldehydes are restricted to a few families such as p-anisaldehyde occurs in the fruits of *Pelea madagascariensis* (Rutaceae), *Agastache rugosa* (Labiatae), leaves of *Magnolia salicifolia* (Magnoliaceae) and also in the essential oils of Vanilla spp. (Orchidaceae), Acacia spp. (Leguminosae), Cassia spp. (Leguminosae), Pinus spp. (Pinaceae), *Pimpinella anisum* (Umbelliferae), *Illicium verum* (Illiciaceae), whereas p-hydroxybenzaldehyde occurs in traces in *Plocama pendula* (Rubiaceae), *Pterocarpus marsupium* (Leguminosae), and asaronaldehyde in the essential oils of Acorus spp. (Motley, T. J., Economic Botany, 48: 397–412, (1994) and Piper spp. (Koul, S. K., Taneja, S. C., Malhotra, S. and Dhar, K. L., Phytochemistry, 32(2): 478–480, (1993)). However, the limited percentage of these substituted phenylaldehydes present in the plant kingdom is not sufficient to fulfill the world demand and as a result, the major amounts of phenylaldehydes are made synthetically.

A number of processes have been proposed to prepare substituted phenylaldehydes such as p-anisaldehyde, dimethoxybenzaldehyde, vanillin, heliotropin, asaronaldehyde etc. For the most part, these methods involves reacting the substituted benzene, such as p-methoxybenzene, 1,2,4-trimethoxybenzene with freshly distilled phosphorus oxychloride ($POCl_3$) in the presence of anhydrous N,N-dimethylformamide (DMF). However, while this Vilsmeier-Haack method has been proven to be useful, they suffer from one or more process deficiencies. For example, some processes of this type necessarily involve resort to sub ambient temperatures, which, of course, involves some considerable process control. In addition, large excesses of DMF and $POCl_3$ must necessarily be employed to carry out the synthesis to obtain appreciable yields and moreover, $POCl_3$ give rise to a violent exothermic reaction leading to obvious problems. Lastly, in some cases, the reaction is effected by the formation of some side reaction products (Toril, S., Uneyama, K. and Ueda, K., J. Org. Chem., 49, 1830–1832 (1984).

Typical prior art refrences include U.S. Pat. Nos. 2,794, 813; 5,358,861; 3,799,940; European Patent No. EP-A 405, 197; Japanese Pat. Nos. 10,754,442A2; 55,87, 739; British Pat. Nos. 417,072; 774,608; 1,092,615; U.S.S.R. Pat. No. 490,793 and German Pat. Nos. 57,808; 207,702.

It therefore becomes an object of the invention to provide rapid and economical process for the preparation of substituted phenylaldehydes from trans and cis-phenylpropenes which further provide commercial utilization of toxic cis-isomer as well as eliminate the above discussed disadvantages and others.

OBJECTIVES OF THE INVENTION

The main object of the present invention is to develop a rapid and economical process for the preparation of useful phenylaldehydes (such as p-methoxybenzaldehyde, vetralaldehyde, asaronaldehyde etc) in one step.

Another object of the invention is to develop a simple process for the preparation of phenylaldehyde in high purity.

Another object of the invention is to develop a simple process for the preparation of phenylaldehyde with minimum or no side product formation such as corresponding acid.

Yet another object of the invention is to develop an easy work-up of the reaction product.

Yet another object of the invention is to develop a simple process for high degree of conversion.

Yet another object of the invention is to develop a process, which does not require anhydrous reaction medium, a condition preferred by industries.

Yet another object of the invention is to develop a simple process which does not require explosive and expensive reagents, hence, capable of undergoing commercial scale production.

Yet another object of the invention is to develop a simple and quick process for the preparation of substituted phenylaldehydes in a short time ranging from 2 to 20 minutes under microwave irradiation.

Yet another object of the invention is to develop a process for the preparation of value added products from toxic compound (such as β-asarone).

Yet another object of the present invention is to explore the possibilities of preparing important aldehydes utilizing otherwise toxic essential oil e.g. crude calamus oil of tetraploid or hexaploid varieties or the other essential oil rich in anethole, isosafrole, methyl isoeugenol (at least above 75% in crude oil) or the like, thereby, enhancing the profitable use thereof.

Yet another object of the present invention is to explore a simple and cheaper starting material in which what ever percentage of cis (toxic) and trans-isomer (non-toxic) exists in crude essential oil or formed during alkaline isomerisation of γ-phenylpropenes (such as methylchavicol, safrole, methyl eugenol etc) are capable of undergoing oxidation into high valued phenylaldehydes otherwise the percentage of cis-isomer higher than a limited amount is not allowed with trans-isomer for commercial use in perfumery, flavour and pharmaceutics.

SUMMARY OF THE INVENTION

In brief, the present invention provides microwave assisted rapid (reaction time less than 20 minutes) and economical process for the preparation of substituted phenylaldehydes from trans and cis-phenylpropene derivatives using meta-periodate and osmium tetraoxide (catalytic amount) as an efficient oxidizing agent in the presence of catalyst namely amberlite IRA-410 and quaternary ammonium salt. It is worthwhile to mention that the conversion of toxic β-asarone (cis-isomer) from *Acorus calamus* or β-asarone (70–94%) rich crude *calamus* oil directly into asaronaldehyde (a versatile drugs precursor) is an economical gain of the above invention since it provides a proper utilization of internationally banned tetraploid and hexaploid varieties derived essential oil of *Acorus calamus*.

DETAILED DESCRIPTION OF THE INVENTION

Accordingly, the present invention provides a microwave assisted rapid and economical process for the preparation of substituted phenylaldehydes from trans and toxic cis-phenylpropenes, a commercial utilization of toxic cis-isomer of the general formula (I), Formula I wherein $R_1$ is —CHO,
  $R_2$, $R_3$, $R_4$, $R_5$, $R_6$ are independently selected from
  i) a hydrogen atom;
  ii) an alkoxy group at least two of $R_2$, $R_3$, $R_4$, $R_5$, $R_6$ being hydrogen atom; or an alkoxy group but one of $R_2$, $R_3$, $R_4$, $R_5$, $R_6$ being methylenedioxy group in combination with either hydroxyl group, an alkoxy group, an alkyl group having at least one carbon atom, an aryl group and a hydrogen atom or an alkoxy group but one of $R_2$, $R_3$, $R_4$, $R_5$, $R_6$ being hydroxyl group in combination with either methylenedioxy group, a hydroxyl group, an alkoxy group, an alkyl group having at least one carbon atom, an aryl group (—$C_6H_5$)or a hydrogen atom;
  iv) a hydroxyl group at least one of $R_2$, $R_3$, $R_4$, $R_5$, $R_6$ being a hydrogen atom in combination with either an alkoxy group, a hydroxyl group, a methylenedioxy group, an alkyl group having at least one carbon atom, an aryl group or a hydrogen atom;
  v) a protected hydroxyl group such as acetyl, benzyl, etc at least one of $R_2$, $R_3$, $R_4$, $R_5$, $R_6$ being a hydrogen atom in combination with either an alkoxy, a hydroxyl group, a methylenedioxy group, an alkyl group having one or more carbon atoms, an aryl group or a hydrogen atom; said substituted phenylaldehydes being from corresponding ($R_2$—$R_3$—$R_4$—$R_5$—$R_6$) phenylpropene derivatives, said process comprising oxidizing phenylpropene derivatives in presence of an oxidizing agent and optionally a co catalyst in a solvent at a mole ratio of 1:1 to 1:12 for a period ranging from 20 seconds to 20 minutes under microwave radiation, removing the solvent under reduced pressure and isolating the product in a conventional manner to obtain a yield between 71 to 82% of substituted phenylaldehydes.

In an embodiment, the solvent used is selected from the group consisting of ether solvent such as tetrahydrofuran, dimethyoxyethane, dioxane; ketonic solvents selected from acetone, ethylmethyl ketone; alcohols selected from methanol, ethanol and in presence of water.

In another embodiment of the invention, the oxidizing agent used is selected from potassium permanganate/base, manganese dioxide/sulphanilic acid, meta-periodate/osmium tetraoxide.

In still another embodiment of the invention, the co catalyst used is selected from amberlite such as amberlite-410, quaternary ammonium salt such as benzyltriethyl ammonium chloride, base such as triethylamine, pyridine.

In yet another embodiment of the invention, the mole ratio of phenylpropene derivatives to oxidizing agent is ranging from 1:1 to 1:6.

In yet another embodiment of the invention, the radiation frequency of microwave used is ranging from 2000 to 2800 MHz.

In yet another embodiment of the invention, the starting material phenylpropene is widely available natural phenylpropanoid.

In yet another embodiment, both isomeric forms (E & Z) of phenylpropene are utilized for phenylaldehyde formation.

In yet another embodiment of the invention, toxic cis-isomer is converted into value added natural aldehyde.

In yet another embodiment, an internationally banned β-asarone from *Acorus calamus* is utilized by its conversion into a useful asaronaldehyde.

In yet another embodiment, the above process is capable of preparing phenylaldehyde derivatives on commercial scale.

In yet another embodiment of the invention, the above process oxidizes crude *calamus* oil of tetraploid or hexaploid varieties or the other essential oil rich in anethole, isosafrole, dimethoxy isoeugenol (at least above 75% in crude oil).

In yet another embodiment of the invention provides a process wherein, the phenylaldehyde derivatives in highest purity without any contamination of corresponding acid and alcohol.

In yet another embodiment, the above process provides phenylaldehyde derivatives in a very short time period ranging from 2–20 minutes.

In yet another embodiment of the invention, the above process allows conducting reaction in aqueous medium, a condition preferred by industries and provides easy work-up of the reaction product.

In yet another embodiment provides a simple process and cheaper starting material, in which what ever percentage of cis (toxic) and trans-isomer (preferred) exists in crude essential oil or formed during alkaline isomerisation of γ-phenylpropenes (such as methylchavicol, safrole, methyl eugenol etc) are oxidized into high valued phenylaldehydes, otherwise higher than the allowed percentage of cis-isomer formed along with the trans-isomer is not allowed for commercial use in perfumery, flavour and pharmaceutics.

In yet another embodiment of the invention provides a process wherein, in the above process for the preparation of some new phenylaldehydes, which are useful as a simple starting material for synthesis of corresponding acids, esters, amides, alcohol, and β-unsaturated aldehyde and are also useful for the dyes, alkaloids, agrochemical etc.

Broadly speaking the invention relates to cis and trans-isomeric forms of ($R_2$—$R_3$—$R_4$—$R_5$—$R_6$)phenylpropene bearing essential oils such as β-asarone, anethole and methyl isoeugenol or the like wherein $R_2$ to $R_6$ equal or different, being hydrogen or hydroxy or acyl or alkyl or methylenedioxy or alkoxy groups or the like, are oxidized under microwave irradiation using meta-periodate/osmium tetraoxide for a reaction time less than 20 minutes in biphasic system comprising a solvent and aqueous phase containing a catalyst and thus high valued industrially important substituted phenylaldehydes such as asaronaldehyde, p-anisaldehyde, vetralaldehyde or the like derivatives are obtained in a single step in high yield varies from 71–82% depending upon the reagent, reaction time, condition and the phenylpropene used, the conversion of toxic β-asarone (cis-isomer) from *Acorus calamus* or β-asarone (70–94%) rich crude *calamus* oil directly into asaronaldehyde (a versatile drugs precursor) is an economical gain of the above invention since well explored *Acorus calamus* (tetraploid and hexaploid varieties) has recently been banned internationally for their use in human consumption.

Accordingly, the present invention provides microwave assisted rapid and economical process for the preparation of substituted phenylaldehydes from trans and toxic cis-phenylpropenes of Formula I, a commercial utilization of toxic cis-isomer wherein $R_1$ is fixed as a —CHO, however, $R_2$, $R_3$, $R_4$, $R_5$, $R_6$ are independently; i) a hydrogen atom; ii) a alkoxy group but at least two of them from $R_2$, $R_3$, $R_4$, $R_5$, $R_6$ are hydrogen atom or a alkoxy group but one methylenedioxy group with combination of either hydroxyl group, alkoxy group, alkyl group having at least one carbon atom, aryl group (—$C_6H_5$) and hydrogen atom or a alkoxy group but one hydroxyl group with combination of either methylenedioxy group, hydroxyl group, alkoxy group, alkyl group having at least one carbon atom, aryl group and hydrogen atom; iii) a methylenedioxy with at least three of them from $R_2$, $R_3$, $R_4$, $R_5$, $R_6$ are combination of either alkoxy, hydroxy group, alkyl group having at least one carbon atom, aryl group and hydrogen atom; vi) a hydroxyl group but one of them from $R_2$, $R_3$, $R_4$, $R_5$, $R_6$ is hydrogen atom with combination of either alkoxy, hydroxyl group, methylenedioxy group, alkyl group having one carbon atom, aryl group and hydrogen atom; vii) a protected hydroxyl group such as acetyl, benzyl, etc but at least one of them from $R_2$, $R_3$, $R_4$, $R_5$, $R_6$ is hydrogen atom with combination of either alkoxy, hydroxyl group, methylenedioxy group, alkyl group having one or more carbon atom, aryl group and hydrogen atom or the like, obtained from corresponding ($R_2$—$R_3$—$R_4$—$R_5$—$R_6$)phenylpropene derivatives (e.g. anethole where $R_2$=$R_3$=$R_5$=$R_6$=H; $R_4$=OMe; methyl isoeugenol where $R_2$=$R_5$=$R_5$=H; $R_3$=$R_4$=OMe and b-asarone where $R_2$=$R_4$=$R_5$—=OMe; $R_3$=$R_6$=H etc) and the above process comprising the steps of (a) providing phenylpropene such as but not limited to 2,4,5-trimethoxyphenylpropene (b-asarone) in the following solvents namely ether such as but not limited to tetrahydrofuran, dimethoxyethane, dioxane, and the like; ketone such as but not limited to acetone, ethylmethyl ketone; alcohol such as but not limited to methanol, ethanol and the like and water; (b) oxidation of phenylpropene derivatives in above solution by adsorbing on oxidizing reagents such as but not limited to meta-periodate/osmium tetraoxide (catalytic amount) and the like to be used in the ratio of 1–12 moles, preferably 1–6 moles per mole of phenylpropene derivative in a short period ranging from 2–20 minutes under microwave irradiation; (c) oxidation step proceeds more smoothly along with higher yield in presence of co-catalyst amberlite such as but not limited to amberlite-410, quaternary animonium salt such as but not limited to benzyltriethylanimonium chloride or base such as but not limited triethylamine, pyridine; (d) filtering the mixture and removing the solvent under reduced pressure, where the product is to be isolated by a conventional manner, i.e. extraction, recrystallization and chromatography and the yield of the product (e.g. 2,4,5-trimethoxybenzaldehyde where $R_1$=—CHO, $R_2$=$R_4$=$R_5$—=OMe; $R_3$=$R_6$=H;

4-methoxybenzaldehyde where $R_1=$—CHO, $R_2=R_3=R_5=R_6=$H; $R_4$—=OMe and 3,4-dimethoxybenzaldehyde where $R_1=$—CHO, $R_2=R_5=R_6=$H; $R_3=R_4$—=OMe etc in the above formula I) varies from 68–81% preferably more in case of meta-periodate/osmium tetraoxide as a oxidizing reagent.

In one more embodiment of the present invention, a simple and cheaper starting material phenylpropene is utilized for high valued phenylaldehyde derivatives, and one step process is described for substituted phenylaldehyde in high purity and yield without contamination of corresponding acid and alcohol.

In another embodiment of the present invention, a simple and quick process for the preparation of substituted phenylaldehydes in a short time ranging from a few seconds to a few minutes under microwave irradiation.

In another embodiment of the present invention, a process for the preparation of value added products from toxic compound (such as β-asarone).

In another embodiment of the present invention, a simple and cheaper starting material in which what ever percentage of cis (toxic) and trans-isomer (non-toxic) exists in crude essential oil or formed during alkaline isomerisation of γ-phenylpropenes (such as methylchavicol, safrole, methyl eugenol etc) are capable of undergoing oxidation into high valued phenylaldehydes otherwise the percentage of cis-isomer higher than a limited amount is not allowed with trans-isomer for commercial use in perfumery, flavour and pharmaceutics.

Plant cells are highly sophisticated chemical factories where a large variety of chemical compounds are synthesized with great precision and ease from simple raw materials at normal pressure and temperature. Beside foods, plant materials/chemicals are used for many purposes for example, for treating medical ailments, dyeing clothes, colouring food items and for perfumery, cosmetics, flavour etc. Flavours represent a growing demand within the food industry. Several methods including chemical synthesis, biotechnology and natural extraction are under progress for the smooth production of aroma chemicals. Some of aromatic phenylaldehydes, mainly produced in plants in response to pathogen attack, possess strong antimicrobial activity due to hydroxy and an aldehyde group attached to the aromatic ring of phenylaldehyde. Therefore, as per applications concern, these phenylaldehydes are not only widely used in fragrances, flavours, cosmetics, liquors, pharmaceuticals but they are also utilized as antibacterials, antifungals, and as biologically active compounds. Moreover, phenylpropenes, produced by plants in high concentration (sometimes unto 95–96%) are also widely used by perfumery, flavour and pharmaceutical industries, e.g. anethole (4-methoxyphenylpropene) is well exploited essential oil which exists in cis- and trans-form (Miraldi, E.; Flavour & Fragrance Journal, 14(6) 379–382 (1999)), but its corresponding phenylaldehydes have more demand, as only trans-anethol is allowed since cis-anethol is possibly considered toxic and hazardous to human beings. On the other side, vanillin (a phenylaldehyde) is one of the most commonly consumed flavour chemicals (5,550 t/a worldwide) (Somogyi, L. P., Chem. Ind. L., 5, 170, (1996). However, the limited percentage and high price of these natural phenylaldehyde led to the necessity of using large amount of synthetic materials. At present, 97% of the world vanilla flavour market is synthetic vanillin and remaining 3% (weight basis) is a natural vanilla extract (Taylor, A. J. and Mottram, D. S., In: Flavour Science, Recent Developments, The Royal Society of Chemistry, Thomas Graham House, Science Park, Milton Road, Cambridge CB4 4WF, UK, 111–137, (1996). Various processes are known for the preparation of phenylaldehydes (Schiraldi, D. A. and Kenvin, J. C., U.S. Pat. No. 5,910,613; and Soma, Y., JP Pat. No. 11049734A2; Kashima, M., Yoshimoto, H., Noda, Y. and Jibiki, H. JP Pat. No. 7330655A2; Kajisori, S., JP Pat. No. 2268130A2; Tanaka, M., Sakakura, T., Wada, H. and Sasaki, Y. JP Pat. No. 3264546A2; Kawamoto, K., Yoshioka, T., Yamagata, H., JP Pat. No. 5087739A2 and Ito, N. and Hasebe, A. JP Pat. No. 11279104A2) using phenyipropenes as a starting material. Considering the cost of starting material and reagents, phenylpropenes are found best suitable and cost effective starting material for the synthesis of substituted phenylaldehydes such as vanillin from isoeugenol, p-methoxybenzaldehyde from anethole and heliotropin from isosafarole (U.S. Pat. Nos. 1,643,804; 2,794,813). However, there is so far no such industrial method available for the preparation of a versatile drug intermediate "2,4,5-trimethoxybenzaldehyde" (a phenylaldehyde) from b-asarone (a toxic phenyipropene). It is worthwhile to mention that the selection of b-asarone for the preparation of asaronaldehyde has several fold benefits such as a simple and cheaper starting material and a proper utilization of internationally banned toxic calamus oil. Since b-asarone has recently been proved to be toxic and carcinogenic (Taylor, J. M., Jones, W. I., Hogan, E. C., Gross, M. A., David, D. A. and Cook, E. L., Toxicol. Appl. Pharmacol., 10: 405 (1967); Keller, K.; Odenthal, K. P. and Leng, P. E., Planta Medica, 1: 6–9 (1985) and Kim, S.C., Liem, A., Stewart, B. C. and Miller, J. A., Carcinogensis, 20(7), 1303–1307 (1999)) and the most affected plant is *Acorus calamus* (family:Araceae) in which percentage of toxic b-asarone depends upon the varieties of A. calamus (Riaz, M., Shadab, Q., Chaudhary, F. M., Hamdard Medicus 38(2): 50–62 (1995) and MeGuffin, M., Hobbs, C., Upton, R. and Goldberg, A., In: American Herbal Products Association's Botanical Safety Handbook, CRC Press, Inc.; Boca Raton, Fla.; USA, 231, (1997)). The content of b-asarone in the triploid variety is 8–19%, while b-asarone reaches upto 96% in the tetraploid and hexaploid varieties (extensively found in Asian countries). In contrast, b-asarone is not found in the diploid variety. As a result, the calamus oil obtained from North American diploid strain (zero, b-asarone) and East European triploid strain (unto 12% b-asarone) are allowed for clinical effectiveness and safety while the calamus oil produced in Asian belt (such as India, Pakistan, Bangladesh, Nepal, Japan and China) has diminished the market potential of calamus oil due to high percentage of b-asarone ranging from 70 to 94% (Mazza, G., J. of Chromatography 328:179–206 (1985); Nigam, M. C., Ateeque, A., Misra, L. N. and Abmad, A., Indian Perfumer 34: 282–285 (1990) and Bonaccorsi, I., Cortroneo, A., Chowdhury, J. U. and Yusuf, M., Essenze Derv. Agrum, 67(4): 392–402 (1997)). Therefore, our objective to utilize toxic b-asarone for value added phenylaldehyde does not provide only economical gain for calamus oil of tetraploid or hexaploid strain but also as a simple and cheaper starting material for the preparation of a natural 2,4,5-trimethoxyphenylbenzaldehyde (asarylaldehyde), a versatile drug intermediate for synthesis of several biologically active compounds (Abmad, S., Wagner, H. and Razaq, S., Tetrahedron, 34 (10): 1593–1594, (1978)) including Makaluvamine-D and Discorhabdin-C marine alkaloids (Sadanandan, E. V., Pillai, S. K., Lakshmikantham, M. V., Billimoria, A. D., Culpepper, J. S. and Cava, M. P. J. Org. Chem., 66: 1800–1805, (1995)).

Phenylpropenes are relatively electron rich (pi bonds) which can be oxidized to corresponding aldehyde with a number of oxidizing agents such as chromic acid (Ger. Pat. No. 576 and U.S. Pat. No. 2,794, 813), manganese dioxide (Br. Pat. No. 774,608), potassium permanganate (Erlenmeyer, Chem. Ber. 9, 273 (1876)), chromyl chloride (U.S. Pat. No. 365,918), air (Ger. Pat. No. 224,071), oxygen (Ger. Pat. No. 150,981), ozonolysis (Ger. Pat. No. 321,567 and C.A., 54,:5538 (1960)), electrolysis (Ger. Pat. No. 92,007), peroxide (Ger. Pat. No. 93,938), nitrobenzene (Brit. Pat. No. 271,819 and U.S. Pat. No. 1,643,804), nitrobenzene (Brit. Pat. No. 285,156) and by several others process.

All the above methods have various limitations, for example, low yield, expensive reagents and formation of unwanted side products. Our initial efforts to oxidize β-asarone by using known oxidizing reagents such as potassium permanganate or manganese dioxide/sulphanilic acid (Br. Pat. No. 774,608)) coupled in microwave to obtain asaronaldehyde is remained unsuccessful due to poor yield with various side product formation (such as asaronic acid). Fortunately, the combination of osmium tetroxide ($OsO_4$) and periodate reagent (Cainelli, G., Contento, M., Manescalchi, F. and Plessi, L, Synthesis, 47–48, (1989)) in microwave is found an effective and high yielding method for preparing asaronaldehyde from toxic β-asarone (Example Ia). In addition, microwave assisted oxidation of phenylpropenes or the like with osmium tetroxide conducting in fuming hood is easy and safe otherwise handling of osmium tetraoxide requires special precaution due to its poisonous nature. After success of β-asarone, oxidation of α-asarone into asaronaldehyde is also found as effective as β-asarone. These experiments gave us idea that geometry (i.e. cis/trans-isomer) of phenylpropene does not effect the yield of final oxidized product. In continuation of this oxidation, *calamus* oil (rich in phenylpropene i.e. 85–90% α/β-asarone) is also capable of undergoing oxidation without any problem in purification or loss in yield since other constituents of *calamus* oil does effect interfere in asaronaldehyde formation (Example 1c). Although, $OsO_4$/$NaIO_4$ is well known system for converting alkene into aldehyde, however, microwave assisted oxidation of phenylpropene has not been reported so far for the preparation of substituted phenylaldehydes especially from toxic isomer of phenylpropene i.e. β-asarone (cis-isomer) or phenylpropene rich crude oil (i.e. crude *calamus* oil). Having successfully achieved an efficient process for asaronaldehyde, we decided to extend the process to convert various phenylpropenes into phenylaldehyde via $OsO_4$/$NaIO_4$ such as anethole into 3,4-dimethoxyisoeugenol into 3,4-dimethoxybenzaldehyde (Example II), 4-methoxybenzaldehyde (Example III) or the like. It is further worthwhile to mention that what ever percentage of cis/trans anethole from methyl chavicol, cis/trans isosafrole from safrole, cis/trans isoeugenol from eugenol or the like obtained during alkaline isomerisation of γ-phenylpropene (allylbenzene) or crude essential oil rich cis/trans phenylpropene (above 70% for industrial scale) can be easily utilized for the formation of corresponding phenylaldehydes. Our present invention is also beneficial to those industries which are engaged in alkaline isomerisation of allylbenzene into trans-phenylpropene for wide scope in flavour, perfumery and pharmaceutical industries, however, formation of cis-phenylpropene along with trans-phenylpropene diminished their applications, since separation of isomers is tedious and expensive on industrial point of view whereas, both isomeric forms can be used for the preparation of high valued phenylaldehydes.

Trans-Phenylpropene

Cis-Phenylpropene

Phenylaldehyde

EXAMPLES

The following examples are given by way of illustration of the present invention and should not be construed to limit the scope of the present invention.

Example I

Reaction: ##STR1##

Figure 1:
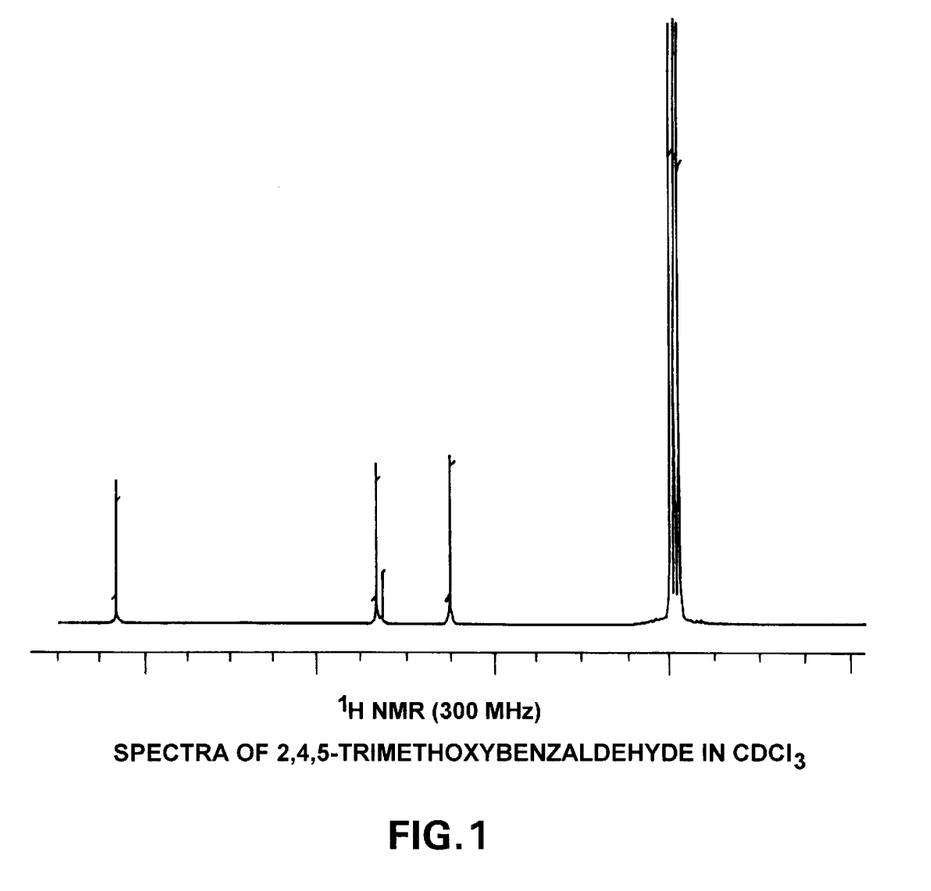
FIG. 1 is $^1$H NMR (300 MHz) spectra of asaronaldehyde (2,4,5-trimethoxybenzaldehyde) (in $CDCl_3$) of the reaction product of Example I containing the compound of Formula I.
Figure 2:
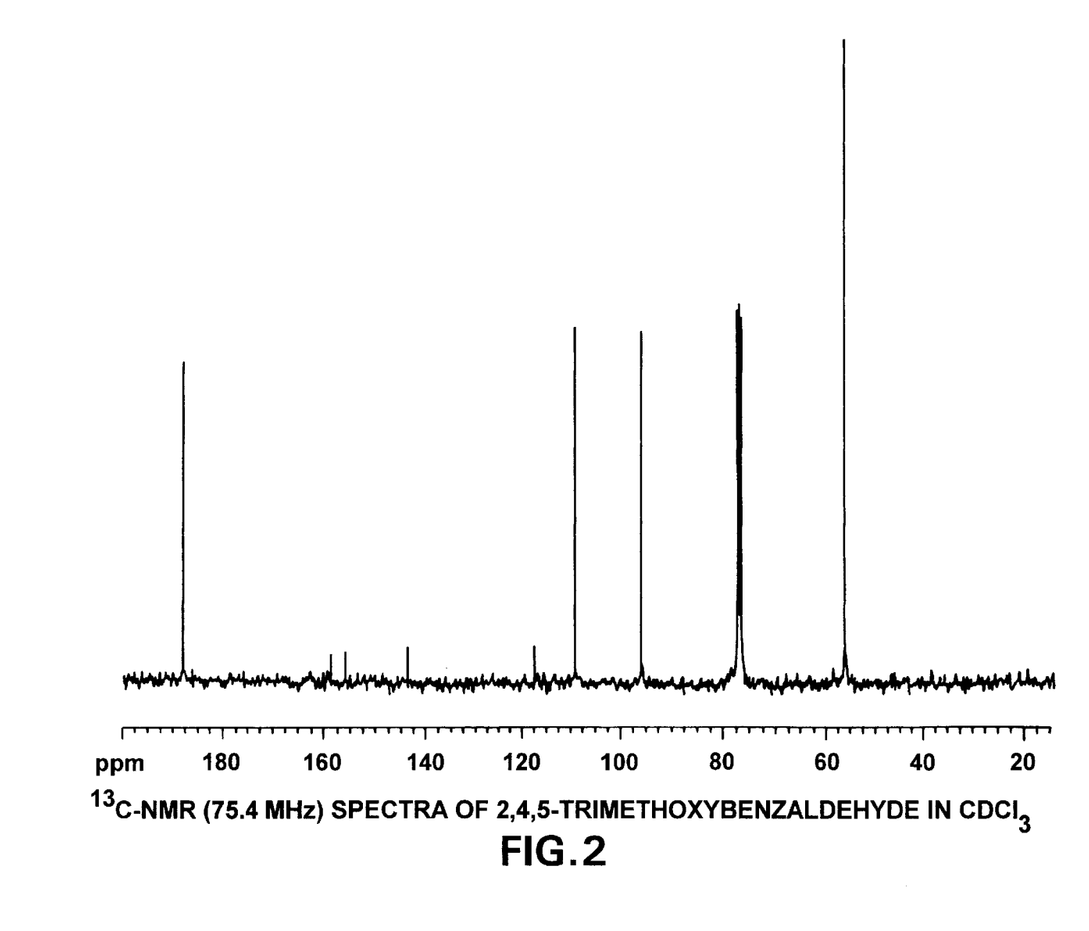
FIG. 2 is $^{13}$C NMR (75.4 MHz) spectra of asaronaldehyde (2,4,5-trimethoxybenzaldehyde) (in $CDCl_3$) of the reaction product of Example I containing the compound of Formula I.
Figure 3:
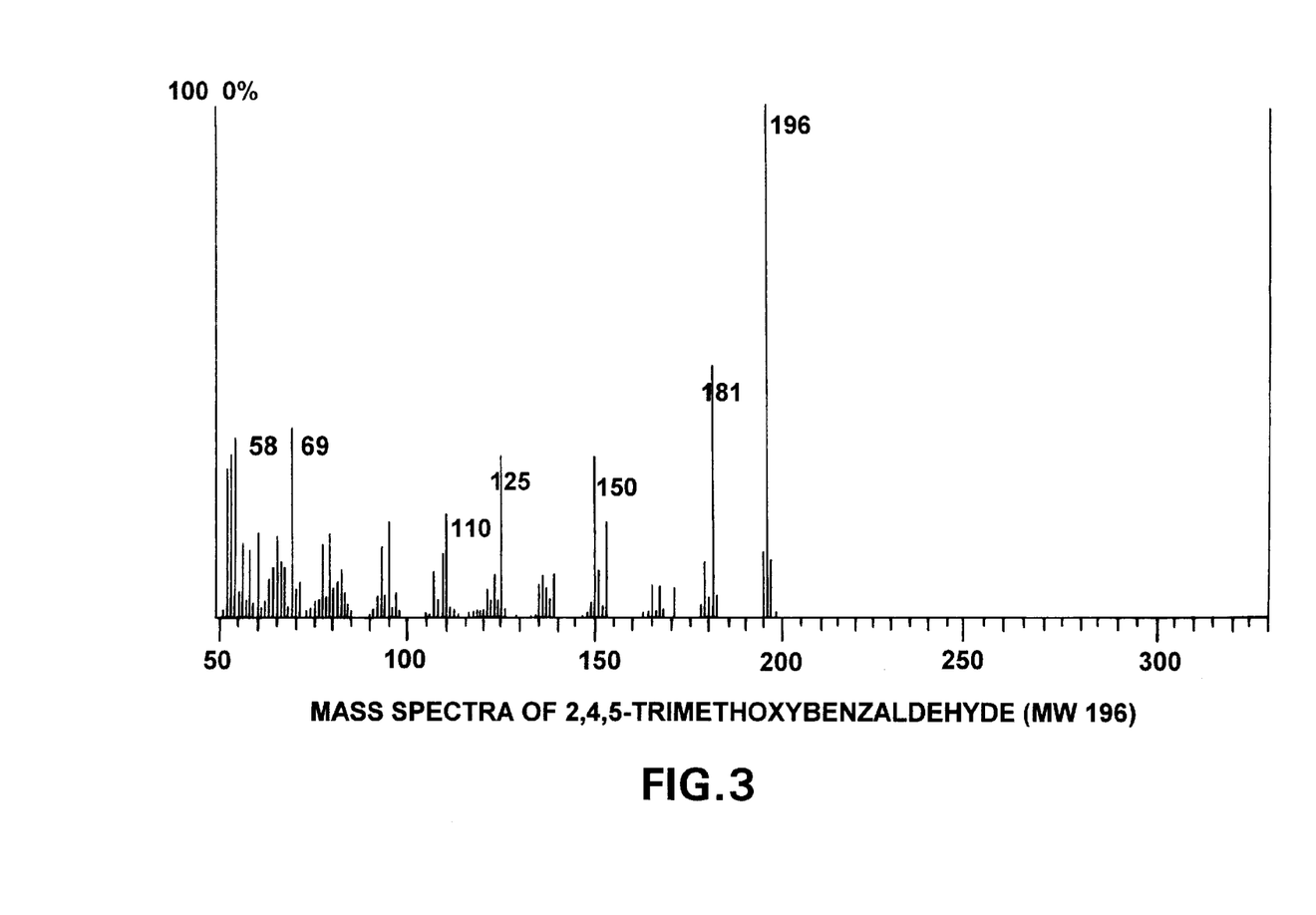
FIG. 3 is the electro spray (ES) mass spectrum of asaronaldehyde (2,4,5-trimethoxybenzaldehyde) (MW 196) of the reaction product of Example I containing the compound of Formula I.

(a) Preparation of asaronaldehyde (2,4,5-trimethoxybenzaldehyde) from β-asarone (by microwave irradiation method): A mixture of β-asarone (3.1 g, 0.015 mmol), catalytic amount of $OsO_4$ (0.04 to 0.002 g), $NaIO_4$ (11.75 g, 0.055 mmol), benzyltriethyl ammonium chloride (catalytic amount) and THF-$H_2O$ (8–10 mL, 4:1) were taken in a 100 ml Erlenmeyer flask fitted with a loose funnel at the top. The flask was shaken well and placed inside a microwave oven operating at medium power level and irradiated for 2–12 minutes in parts. After completion of the reaction (monitored by TLC), the contents of the flask were poured into chloroform and passed through a bed of Celite and further washed with chloroform. The filtrate and washings were combined and the chloroform layer were washed with sodium thiosulphate to destroy the excess periodate. The chloroform layers were then combined and washed with saturated sodium chloride (3×15 m), dried over anhydrous sodium sulphate and filtered. The solvent was removed to afford a crude solid product which was recrytallised with water to afford 2.39 g (82%) of asaronaldehyde as a feathery white needles, $R_f$ (0.34 in 28% ethylacetate in hexane); mp 114° C. (lit. mp 114° C.); IR (film) vmax 1662 (carbonyl group), 1620, 1518, 1481, 1419, 1361, 1300, 1278, 1222, 1199, 1138, 1025, 865 cm$^{-1}$; $^1$H NMR δ 10.32 (1H, s, CHO), 7.33 (1H, s, 6H), 6.50 (1H, s, 3H), 3.98 (3H, s, 2-OCH$_3$), 3.93 ((3H, s, 4-OCH$_3$), 3.88 (3H, s, 5-OCH$_3$); $^{13}$C NMR δ 187.96 (CHO), 158.60 (C-2), 155.76 (C-4), 143.56 (C-5), 117.35 (C-1), 109.03 (C-6), 56.19 (2-OCH$_3$, 4-OCH$_3$ and 5-OCH$_3$); EIMS m/z 196 [M]$^+$ (100), 181 (49), 150 (32), 125 (33), 110(23), 69 (37).

(b) Asaronaldehyde from α-asarone (by conventional method): A solution of OsO$_4$ (0.065 g, 0.25 mmol) in water (2 mL) was added dropwise to ice cold solution of α-asarone (0.624 g, 0.003 mole) (procured from Sigma) in THF-H$_2$O (25 mL, 4:1) over a period of 5 min with constant stirring. After 20 min at 0–5° C., finely powdered NaIO$_4$ (2.35 g, 0.011 mole) was added in parts and reaction mixture was stirred for 4–6 hr at room temperature. After completion of reaction (monitored by TLC), the precipitated sodium iodate was filtered and the filtrate was washed with CH$_2$Cl$_2$. The combined organic layers were washed with 10% solution of sodium bisulphite (to destroy the excess of sodium metaperiodate), saturated brine and dried (Na$_2$SO$_4$). Evaporation of the solvent furnished a crude mixture, which was loaded on silica gel column, and the column was eluted with an increasing amount of hexane/ethyl acetate (95:5 to 70:30). The fractions were monitored on TLC plate and the desired fractions were combined and solvent was removed under vacuum to afford 0.49 g (84%) as a white solid; mp 114° C. The physical and spectral data was found similar as above (Example I).

(c) Preparation of asaronaldehyde from crude *calamus* oil: The rhizomes of '*Acorus calamus* Linn was collected in March–April 1999 from Palampur (H.P.) and was confirmed by comparison with the specimen (IHBT no. 1066) kept in the herbarium of our Institute. The hydrodistillation of rhizomes of *Acorus calamus* gave pungent smelling oil in 1.7% yield (w/w) with a presence of β-asarone (85%) and (α-asarone (3–4%) (by GC) and used directly for oxidation step. A mixture of pale yellow crude *calamus* oil (9.00 g), catalytic amount of OsO$_4$ ((0.08 to 0.002 g), NaIO$_4$ (50 to 55 g) and dioxane-H$_2$O(50–60 mL or more, 4:1) were taken in a 500 ml beaker fitted with a loose watch glass at the top. The beaker was placed inside a microwave oven operating at medium power level and irradiated for 3–16 minutes in parts. After completion of the reaction (monitored by TLC), the contents of the beaker were filtered and washed with ethyl acetate. The ethylacetate layers were washed with water, aqueous sodium bisulphite (to destroy the excess periodate) and brine, dried over (anhydrous sodium sulphate) and filtered. The solvent was removed under reduced pressure and crude solid was recrystallised with hexane and chloroform to obtain 5.66 g (76%, based on % of α and β-asarone in crude *calamus* oil) of pure asaronaldehyde as a white solid; mp 114° C. The physical and spectral data was found similar as above (Example I).

Example II

Preparation of 3,4-dimethoxybenzaldehyde from methyl isoeugenol (by microwave method): The starting material methyl isoeugenol (3,4-dimethoxy phenylpropene) can be easily prepared by fast 0-methylation of cheaper and easily available isoeugenol (3-methoxy-4-hydroxy-phenylpropene) for which a mixture of isoeugenol (2.46 g, 0.015 mole), dry dimethyl sulphate (1.8 g, 0.14 mole), anhydrous potassium carbonate (6 g, 0.062 mole) and dry acetone (15–20 mL) was irradiated in a microwave oven for 8–10 minutes in parts. After completion of reaction (monitored by TLC) the contents of the flask were poured into ice water. The product was taken in ether (50–60 mL) and the ether layer was washed with dilute hydrochloric acid, saturated sodium bicarbonate and brine respectively and dried over anhydrous sodium sulphate and filtered. The solvent was removed under reduced pressure to afford a desired product methyl isoeugenol (2.32 g, 87% yield) which was used directly for next step.

A solution of OsO$_4$ (0.006–0.008 g), methyl isoeugenol (0.53 g, 0.003 mole), finely powdered NaIO4 (2.35 g, 0.011 mole), amberlite IRA-410 (0.1 g) in THF-H$_2$O (25 mL, 4:1) was irradiated in a microwave oven for 3–11 minutes. After completion of reaction (monitored by TLC), the precipitated sodium iodate was filtered and the filtrate was washed with CH$_2$Cl$_2$. The combined organic layers were washed with sodium thiosulphate (to destroy the excess of sodium metaperiodate), saturated brine and dried over Na$_2$SO$_4$. Evaporation of the solvent furnished a crude mixture, which was loaded on silica gel column, and the column was eluted with an increasing amount of hexane/ethyl acetate (95:5 to 70:30). The fractions were monitored on TLC plate and the desired fractions were combined and solvent was removed under vacuum to afford 3,4-dimethoxybenzaldehyde in 79% yield as a solid; $^1$H NMR δ 9.86 (1H, s, CHO), 7.45 (1H, s, 6H), 7.41 (1H, s, 2H), 6.98 (1H, s, 5H), 3.97 (3H, s, 4-OCH$_3$), 3.95 (3H, s, 3-OCH$_3$). The remaining physical and spectral data was found similar as reported.

Example III

Preparation of 4-methoxybenzaldehyde from Anethole (by Microwave Method):

A solution of OsO$_4$ (0.004–0.007 g), anethole (2.22 g, 0.015 mole), finely powdered NaIO$_4$ (9.0 g, 0.044 mole) in THF-H$_2$O(20–25 mL) was irradiated in a microwave oven for 2–8 minutes in parts. The precipitated sodium iodate was filtered and the filtrate was washed with CH$_2$Cl$_2$. The combined organic layers were washed with sodium thiosulphate, brine and dried over Na$_2$SO$_4$. Evaporation of the solvent furnished a crude mixture, which was loaded on silica gel column and the column was eluted with increasing amount of hexane/ethyl acetate (98:2 to 80:20). The fractions were monitored on TLC plate and the desired fractions were combined and solvent was removed under vacuum to afford 4-methoxybenzaldehyde in 71% yield as a sweet smell liquid; $^1$H NMR δ 9.95 (1H, s, CHO), 7.82 (1H, s, 6H), 7.79 (1H, s, 2H), 6.99 (1H, s, 5H), 6.96 (1H, s, 5H), 3.84 (3H, s, 4-OCH$_3$). The remaining physical and spectral data was found similar as reported and yield was found less may be due to evaporation of anethole during microwave irradiation.

The Main Advantages of the Present Invention are
1. A simple and economical industrial process to convert phenylpropene derivatives into corresponding phenylaldehyde in one step.
2. A simple process to convert phenylpropene derivatives into corresponding phenylaldehyde in high yields.
3. A process to convert an internationally banned toxic compound β-asarone of *calamus* oil or cis anethol or the like into useful products.

4. Preparation of phenylaldehyde as an inexpensive and simple starting material for corresponding acid, ester, and alcohol or the like and are also useful for α,β-unsaturated aldehyde and the dyes, alkaloids, agrochemicals etc.
5. The present chemical process can increase the price of *calamus* oil by its conversion into asaronaldehyde, otherwise, *calamus* oil of tetraploid or hexaploid varieties (distributed extensively in Asian origin) has very low price in comparison to the oil of diploid and triploid (distributed in American or European origin) varieties.
6. A simple process by which any kind of phenylpropene can be converted into corresponding aldehyde in a shorter time ranging from 2–20 seconds.
7. A simple process for preparation of phenylaldehyde which does not require anhydrous reaction medium, a condition preferred by industries.
8. A simple process for the preparation of value added products from toxic compounds such as β-asarone few seconds to minutes under microwave irradiation.
9. A simple process for preparation of phenylaldehyde in which what ever percentage of cis (toxic) and trans-isomer (preferred) exists in crude essential oil or formed during alkaline isomerisation of γ-phenylpropenes (such as methylchavicol, safrole, methyl eugenol etc) are capable of undergoing oxidation into high valued phenylaldehydes otherwise the percentage of cis-isomer higher than a limited amount is not allowed with trans-isomer for commercial use in perfumery, flavour and pharmaceutics.

What is claimed is:

1. A microwave assisted rapid and economical process for the preparation of substituted phenylaldehyde of general formula (I) from substituted trans and toxic cis-phenyipropene, thereby commercially utilizing the toxic cis-isomer of phenylpropene, (I)

wherein $R_1$=—CHO, $R_2$, $R_3$, $R_4$, $R_5$, $R_6$ are independently selected from
  i) a hydrogen atom;
  ii) an alkoxy group wherein at least two of $R_2$, $R_3$, $R_4$, $R_5$, $R_6$ being a hydrogen atom; or an alkoxy group but one of $R_2$, $R_3$, $R_4$, $R_5$, $R_6$ being a methylenedioxy group in combination with either a hydroxyl group, an alkoxy group, an alkyl group having at least one carbon atom, an aryl group and a hydrogen atom or an alkoxy group but one of $R_2$, $R_3$, $R_4$, $R_5$, $R_6$ being a hydroxyl group in combination with either a methylenedioxy group, a hydroxyl group, an alkoxy group, an alkyl group having at least one carbon atom, an aryl group or a hydrogen atom;
  iii) a methylenedioxy group wherein at least three of $R_2$, $R_3$, $R_4$, $R_5$, $R_6$ being in combination with either an alkoxy group, a hydroxy group, an alkyl group having at least one carbon atom, an aryl group or a hydrogen atom;
  iv) a hydroxyl group at least one of $R_2$, $R_3$, $R_4$, $R_5$, $R_6$ being a hydrogen atom in combination with either an alkoxy group, a hydroxyl group, a methylenedioxy group, an alkyl group having at least one carbon atom, an aryl group or a hydrogen atom;
  v) a protected hydroxyl group wherein at least one of $R_2$, $R_3$, $R_4$, $R_5$, $R_6$ being a hydrogen atom in combination with either an alkoxy, a hydroxyl group, a methylenedioxy group, an alkyl group having one or more carbon atom, an aryl group or a hydrogen atom; said process comprising steps of:
    a) oxidizing said substituted phenyipropene in the presence of an oxidizing agent and optionally with a co-catalyst in a solvent at a mole ratio of 1:1 to 1:12 for a period ranging from 20 seconds to 20 minutes under microwave irradiation,
    b) filtering the reaction mixture of step (a) and washing the residue with an organic solvent,
    c) washing the organic solution of step (b) with aqueous sodium bisulphite or sodium thiosulphate followed by brine and water,
    d) drying the organic layer of step (c) over anhydrous sodium sulphate, filtering and evaporating to dryness to remove completely the solvent to obtain a residue, and
    e) purifying the residue of step (d) by recrystallization or column chromatography to obtain the required substituted phenylaldehye of general formula (I).

2. A process as claimed in claim 1 wherein the solvent is selected from the group consisting of tetrahydrofuran, dimethyoxyethane, dioxane, acetone, ethylmethyl ketone, methanol diluted with water and ethanol diluted with water.

3. A process as claimed in claim 1 wherein the oxidizing agent is selected am potassium pennanganate/base, manganese dioxide/sulphanilic acid, or meta-periodate/osinium tetraoxide.

4. A process as claimed in claim 1 wherein the co-catalyst is selected from amberlite resins, benzyltriethyl ammonium chloride, triethylamine, or pyridine.

5. A process as claimed in claim 1 wherein the mole ratio of substituted phenylpropene to oxidizing agent ranges from 1:1 to 1:6.

6. A process as claimed in claim 1 wherein the microwave radiation frequency used is in the range of 2000 to 2800 MHz.

7. A process as claimed in claim 1 wherein the phenylpropene is phenylpropanoid.

8. A process as claimed in claim 1 wherein both isomeric forms of the phenylpropene are utilized for phenylaldehyde formation.

9. A process as claimed in claim 1 wherein said toxic cis-isomer is convened into the substituted phenylaldehyde of general formula (I) which is a natural aldehyde.

10. A process as claimed in claim 1 wherein said toxic cis-isomer is toxic cis-phenylpropene β-asarone from *Acorns calamus* and is converted into the substituted phenylaldehye of general formula (I) which is asaronaldehyde.

11. A process as claimed in 1 wherein, said process is capable of preparing said substituted phenylaldehyde on a commercial scale.

12. A process as claimed in claim 11 wherein step (a) is conducted in an aqueous medium and provides easy work-up.

13. A process as claimed in claim 1 comprising the oxidation of said substituted trans and cis-pbatylpropene present in *calmus* oil or other essential oils or formed during alkaline isomerization of γ-phenylpropenes.

14. A process as claimed in claim 1 wherein said substituted phenylaldehyde is obtained in high purity without any contamination of corresponding acid and alcohol.

15. A process as claimed in claim 1 wherein the time period in step (a) is 2–20 minutes.

16. A process as claimed in claim 1 wherein a mixture of the trans- and cis-isomers are converted to the substituted phenyldehyde regardless of the proportions of said isomers in said mixture.

17. A process as claimed in claim 1 wherein the substituted phenylaldehyde prepared the process is useful as a simple starting material for synthesis of corresponding acids, esters, amides, alcohols, β-unsaturated phenylaldehyde and is used in the preparation of dyes, alkaloids, and agrochemicals.

18. A process as claimed in claim 1, wherein the substituted phenylaldehyde is selected from the group consisting of asaronaldehyde, asarylaldehyde, 4-methoxybenzaldehyde and 3,4-diinethoxybenzaldehyde.

* * * * *